(12) United States Patent
Lee

(10) Patent No.: US 7,511,291 B2
(45) Date of Patent: Mar. 31, 2009

(54) INFRARED RAY GENERATOR

(75) Inventor: Chyi-Ran Lee, Taipei (TW)

(73) Assignee: WS Far IR Medical Technology Co., Ltd., Taipei (TW)

( * ) Notice: Subject to any disclaimer, the term of this patent is extended or adjusted under 35 U.S.C. 154(b) by 308 days.

(21) Appl. No.: 11/480,950

(22) Filed: Jul. 6, 2006

(65) Prior Publication Data

US 2008/0073594 A1    Mar. 27, 2008

(30) Foreign Application Priority Data

May 11, 2006    (TW) .............................. 95116760 A

(51) Int. Cl.
*H05B 3/14* (2006.01)

(52) U.S. Cl. .............................. 250/504 R; 250/504 H; 250/495.1; 338/225; 607/100; 219/553; 252/502

(58) Field of Classification Search .............. 250/504 R, 250/504 H, 495.1; 338/225; 607/100; 219/553; 252/502

See application file for complete search history.

(56) References Cited

U.S. PATENT DOCUMENTS

| 4,518,851 | A | * | 5/1985 | Oppitz | 219/549 |
| 4,645,913 | A | * | 2/1987 | Oppitz | 219/549 |
| 4,722,853 | A | * | 2/1988 | Batliwalla et al. | 427/256 |
| 4,749,981 | A | * | 6/1988 | Yui et al. | 338/225 |
| 5,221,828 | A | * | 6/1993 | Basheer et al. | 219/202 |
| 6,086,791 | A | * | 7/2000 | Miller | 252/511 |
| 6,818,156 | B1 | * | 11/2004 | Miller | 252/511 |
| 6,922,017 | B2 | * | 7/2005 | Konishi et al. | 313/623 |

* cited by examiner

*Primary Examiner*—Jack I Berman
(74) *Attorney, Agent, or Firm*—Rosenberg, Klein & Lee

(57) ABSTRACT

An IR generator comprises a base body, an electro-thermal body and an IR emitting body. The electro-thermal body is located on the base body and generates heat when electric power is supplied. The IR emitting body is located on the electro-thermal body and emits IR when absorbing the heat. The IR emitting body comprises an IR coating. The composition of the IR coating comprises graphite and carbon black. The ratio between the graphite and the carbon black is about 1:1-1:2.

11 Claims, 2 Drawing Sheets

INFRARED RAY GENERATOR

BACKGROUND

1. Field of Invention

The present invention relates to a radiation generator. More particularly, the present invention relates to an infrared ray (IR) generator.

2. Description of Related Art

IR is one type of electromagnetic wave. The wavelength range of IR is about 0.75-1000 µm. Based on the wavelength range, IR can be divided into near-IR, middle-IR and far-IR. The wavelength range of near-IR is about 0.75-1.5 µm. The wavelength range of middle-IR is about 1.5-5.6 µm. The wavelength range of far-IR is about 5.6-1000 µm. Scientific research discovers that IR has curative effect, especially far-IR with wavelength range of 6-14 µm. Because far-IR with such wavelength range can resonate with water molecules inside organisms, far IR can be absorbed by organisms easily and promote the growing of organisms. Therefore, far-IR with wavelength range of 6-14 µm is called bio-spectrum. More and more people start to study medical application of IR, and more and more IR relevant products are commercialized in the market.

IR generator for medical application is manufactured by coating an IR coating on an electro-thermal body, which generates heat. The IR coating generates IR when absorbing heat generated by electro-thermal body. Human body is irradiated by IR emitted from the IR coating to achieve the curative effect.

The IR coating of the traditional IR generator has multiple components. Several metal oxides are mixed to form the traditional IR coating. Some metal oxides are rare and expensive. Therefore, the material cost of the traditional IR, coating is high and the price is expensive. Moreover, it is very difficult to mix chemically and physically different metal oxides very well. Therefore, the manufacturing processes of the traditional IR coating are complex and the production cost thereof is high.

SUMMARY

It is therefore an aspect of the present invention to provide an IR generator and a composition of an IR coating thereof. The IR coating used in the IR generator has excellent emissivity in IR wavelength range, especially in far-IR. Moreover, the composition of the IR coating is simple, easy to make and has low production cost. Besides, the material cost of the IR coating is also very cheap, which is only one-tenth of the material cost of traditional IR coating.

In accordance with the foregoing and other aspects of the present invention, an IR generator comprises a base body, an electro-thermal body and an IR emitting body. The electro-thermal body is located on the base body and generates heat when electric power is supplied. The IR emitting body is located on the electro-thermal body and emits IR when absorbing the heat. The IR emitting body comprises an IR coating. The composition of the IR coating comprises graphite and carbon black. The ratio between the graphite and the carbon black is about 1:1-1:2.

In accordance with the foregoing and other aspects of the present invention, a composition of an IR coating is provided. The composition of the IR coating comprises graphite and carbon black. The ratio between the graphite and the carbon black is about 1:1-1:2.

In conclusion, the IR generator of the invention uses carbon having high IR emissivity as the IR coating. The component of IR coating comprises two allotropes of carbon, graphite and carbon black. Although graphite with high conductivity was considered not suitable to be coated on the electro-thermal body of the IR generator before, conductivity of graphite can be decreased by mixing with carbon black in the ratio of about 1:1-1:2. In the ratio, the carbon black is not easily deteriorated by oxidation.

In order to obtain high IR emissivity, several metal oxides are used in traditional IR generator as the IR coating. Compared to traditional IR generator, the IR generator of the invention can obtain high IR emissivity by using only graphite and carbon black as the IR coating. The IR coating of the invention is easy to produce, so the production cost is low. Moreover, the material cost of the IR coating in the invention is also very low and is only one-tenth of the material cost of the traditional IR coating.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
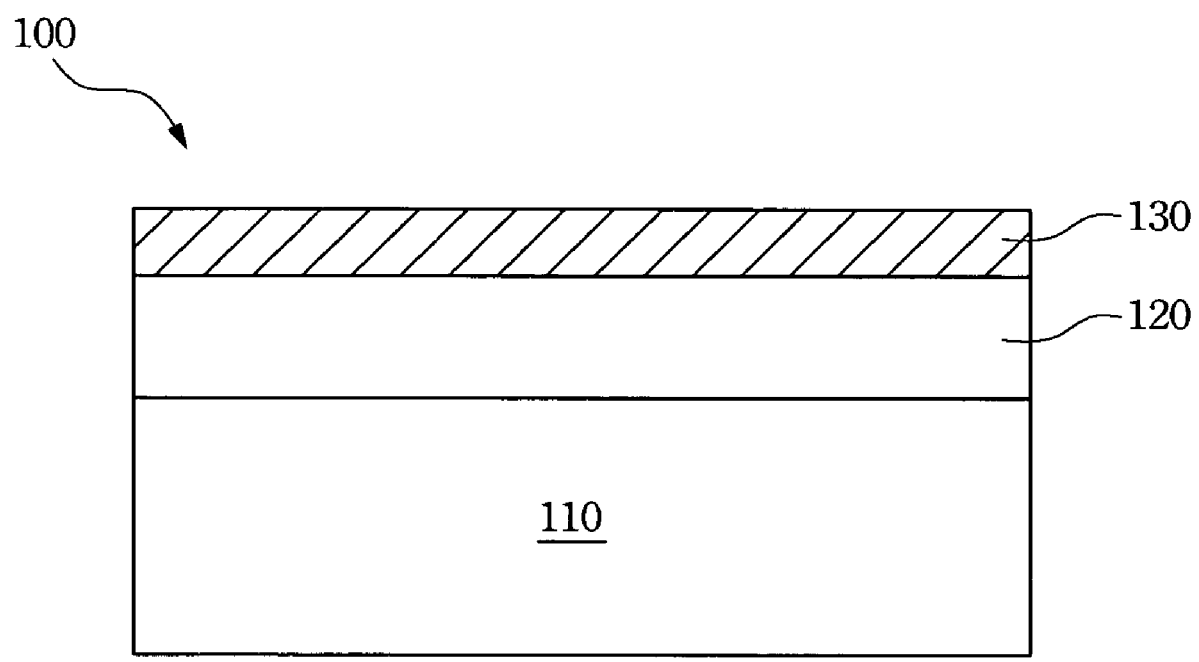
FIG. 1 is a diagram of an IR generator according to a preferred embodiment of the invention.

Carbon has high IR emissivity. Many allotropes of carbon have IR emissivity higher than 90%. Graphite, one type of allotropes of carbon, has IR emissivity up to 98% at the temperature of 20° C. Because carbon has such high IR emissivity, the invention tries to use carbon to produce an IR coating of an IR generator.

Although graphite has almost the highest IR emissivity among all allotropes of carbon, graphite causes electric leakage when coated on an electro-thermal body of an IR generator because of high conductivity of graphite. Therefore, graphite alone is not suitable to be an IR coating of an IR generator.

Carbon black, another allotrope of carbon, also has high IR emissivity. The IR emissivity of the carbon black is up to 95% at the temperature of 20° C. Carbon black is non-conductive, so it won't cause electric leakage when coated on an electro-thermal body of an IR generator. However, carbon black is easily deteriorated by oxidation, so it is also not a proper material to be an IR coating of an IR generator.

Finally, carbon black and graphite are mixed to form an IR coating. With the addition of carbon black, the percentage of graphite amount in the IR coating is decreased and thus the conductivity of the coating is reduced.

TABLE 1 the conductivity test result of IR coatings with different mixing ratios of graphite and carbon black

| Sample | Graphite (%) | Carbon black (%) | Resistance reduction (ohm) of the electro-thermal body | Conductivity |
|---|---|---|---|---|
| 1 | 100 | 0 | 175 | Yes |
| 2 | 70 | 30 | 40 | Yes |

TABLE 1-continued the conductivity test result of IR coatings with different mixing ratios of graphite and carbon black

| Sample | Graphite (%) | Carbon black (%) | Resistance reduction (ohm) of the electro-thermal body | Conductivity |
|---|---|---|---|---|
| 3 | 50 | 50 | 0 | No |
| 4 | 30 | 70 | 0 | No |

Table 1 is the conductivity test result of IR coatings with different mixing ratios of graphite and carbon black. In the test method, IR coatings with different mixing ratios of graphite and carbon black are separately coated on an electro-thermal body. The resistance of the electro-thermal body is 340 ohms. After the electro-thermal body is coated with an IR coating, the resistance value of the electro-thermal body will decrease because of the conductivity of the IR coating. Therefore, the conductivity of the IR coating can be determined by measuring the resistance reduction of the electro-thermal body.

In the test of sample 1 in table 1, graphite is not mixed with carbon black in the IR coating, and the IR coating has high conductivity. The high conductivity of the IR coating reduces the resistance of the electro-thermal body. Therefore, the current amount into the electro-thermal body increases and thus the temperature of the electro-thermal body increases. Finally, the electro-thermal body is broken because the electro-thermal body cannot withstand such high temperature. In the test of sample 2, carbon black is added to the IR coating and mixed with graphite. The added carbon black apparently decreases the conductivity of the IR coating. Although the electro-thermal body can still be functional, there are some sparks resulted from short circuit observed on the electro-thermal body. Therefore, either sample 1 or sample 2 is not suitable to be the IR coating for the IR generator. In the tests of sample 3 and sample 4, with the increase of the carbon black amount percentage in the coating, the conductivity of the coating is greatly decreased. Moreover, the existence of graphite in the coating also reduces the oxidizing ability of carbon black. In conclusion, when the ratio of the graphite and the carbon black in the IR coating is about 1:1-1:2, which is closed to the mixing ratio of sample 3 and sample 4, the IR coating is non-conductive and hardly deteriorated by oxidation. Therefore, the IR coating with such mixing ratio is quite suitable be used in the IR generator.

FIG. 1 is a diagram of an IR generator according to a preferred embodiment of the invention. The IR generator 100 comprises a base body 110, an electro-thermal body 120 and an IR emitting body 130. The electro-thermal body 120 is located on the base body 110. The electro-thermal body 120 generates heat when electric power is supplied. The IR emitting body 130 is located on the electro-thermal body 120. The IR emitting body 130 emits IR when absorbing the heat generated from the electro-thermal body 120. The IR emitting body 130 comprises an IR coating. The composition of the IR coating comprises graphite and carbon black. The ratio of the graphite and the carbon black in the IR coating is about 1:1-1:2.

The base body 110 needs to withstand high temperature and cannot be deformed at high temperature. The material of the base body 110 is preferably rigid or half-rigid temperature-withstand insulating material, such as ceramics, silicon carbide, glass, mica, temperature-withstand insulating plastic material. In FIG. 1, the shape of the base body 110 is flat plate. However, the base body 110 is not limited to flat plate and can be other shapes, such as a tube, a sphere or other suitable shapes. The electro-thermal 120 can be an electro-thermal film covering the base body 110 as shown in FIG. 1. In another embodiment, the electro-thermal body 120 can also be a device made by semiconductor-like self-heating material, such as a silicon carbide resistance. In still another embodiment, the electro-thermal body 120 can be a buried electro-thermal wire or an electro-thermal tube. The IR emitting body 130 can be formed on the thermal-electron body 120 by means of brushing, painting, coating or adhering. Except graphite and carbon black, the composition of the IR coating of the IR emitting body 130 further comprises an adhesive agent to increase the adhesive ability of the IR coating on the electro-thermal 120. The adhesive agent can be a silicon-containing organic or inorganic adhesive agent.

Figure 2:
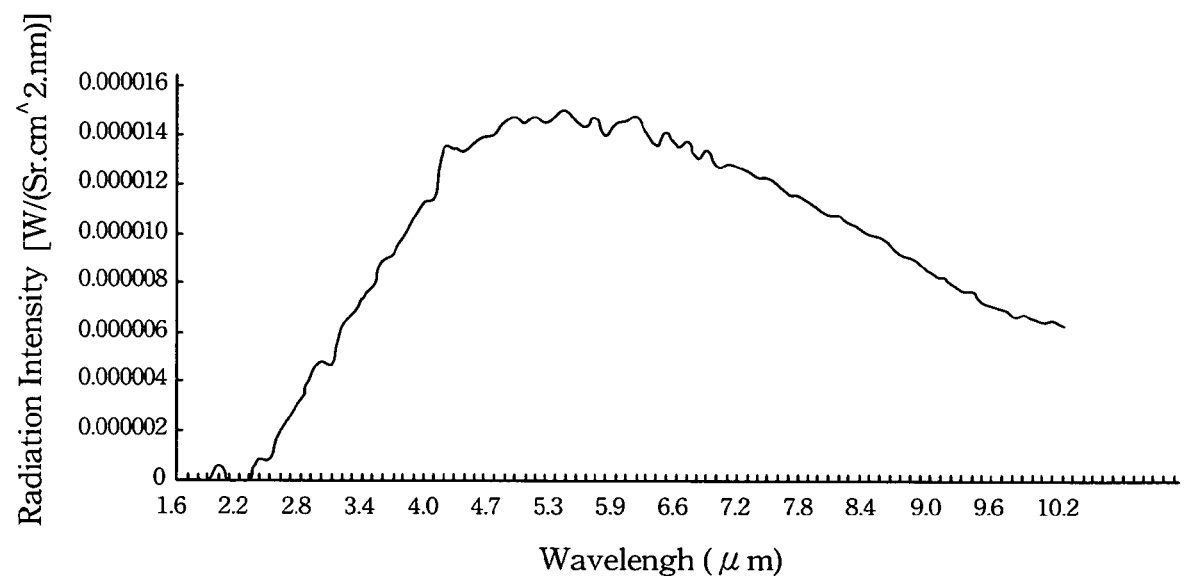
FIG. 2 is an IR emitting spectrum according to a preferred embodiment of the invention.

FIG. 2 is an IR emitting spectrum according to a preferred embodiment of the invention. The IR emitting spectrum is obtained by an IR radiometer at room temperature of 22° C. The measuring method used here is radiometric method. In FIG. 2, the IR generator of the invention has high emissivity in the wavelength range of IR, especially in Far-IR, which has curative effect. The emitting wavelength range shown in the spectrum is about 2.2-10.2 μm. The position of the peak in the spectrum is at about 5.5 μm. The spectrum only shows wavelength below 10.2 μm. However, the IR generator of the invention still has emission at wavelength higher than 10.2 μm. The actual wavelength range of IR emitted by the R generator of the invention is about 3-25 μm.

Accordingly, the present invention has the following advantages.

(1) The composition of the IR coating of the invention is simple, easy to produce and has low production cost.

(2) The IR coating of the IR generator of the invention has excellent emissivity in IR wavelength range, especially in far-IR. Moreover, the material cost of the IR coating of the invention is only one-tenth of the material cost of traditional IR coating.

The preferred embodiments of the present invention described above should not be regarded as limitations to the present invention. It will be apparent to those skilled in the art that various modifications and variations can be made to the present invention without departing from the scope or spirit of the invention. The scope of the present invention is as defined in the appended claims.

What is claimed is:

1. An IR generator, comprising:
    a base body;
    an electro-thermal body located on the base body, wherein the electro-thermal body generates heat when electric power is supplied; and
    an IR emitting body located on the electro-thermal body, wherein the IR emitting body emits IR when absorbing the heat, and the IR emitting body comprises an IR coating, wherein the composition of the IR coating comprises graphite and carbon black and the ratio between the graphite and the carbon black is about 1:1-1:2.

2. The IR generator of claim 1, wherein the IR coating comprises an adhesive agent to adhere the IR coating to the electro thermal body.

3. The IR generator of claim 2, wherein the adhesive agent is a silicon-containing organic adhesive agent.

4. The IR generator of claim 2, wherein the adhesive agent is a silicon-containing inorganic adhesive agent.

5. The IR generator of claim 1, wherein the wavelength range of IR emitted by the IR coating is about 3-25 μm.

6. The IR generator of claim 1, wherein the material of the base body is rigid or half-rigid temperature-withstand insulating material.

7. The IR generator of claim 1, wherein the material of the base body is ceramics, silicon carbide, glass, mica, temperature-withstand insulating plastic material.

8. The IR generator of claim 1, wherein the material of the electro-thermal body is semiconductor-like self-heating material.

9. The IR generator of claim 8, wherein the electro-thermal body is a silicon carbide resistance.

10. The IR generator of claim 1, wherein the electro-thermal body is a buried electro-thermal wire or an electro-thermal tube.

11. The IR generator of claim 1, wherein the IR emitting body is formed on the thermal-electron body by means of brushing, painting, coating or adhering.

* * * * *